United States Patent
Lee et al.

(10) Patent No.: US 10,221,152 B2
(45) Date of Patent: Mar. 5, 2019

(54) USAGE OF MYCOPHENOLATE MOFETIL OR SALT THEREOF IN PREPARING DRUG FOR RESISTING AGAINST INFLUENZA VIRUS

(71) Applicant: GIANT FORCE TECHNOLOGY CORPORATION, New Taipei (TW)

(72) Inventors: An-Rong Lee, Taipei (TW); Chi-Hong Chu, Taipei (TW); Wen-Liang Chang, Taipei (TW); Chen-Wen Yao, Taipei (TW); Wen-Hsin Huang, Taipei (TW); Li-Heng Pao, Taipei (TW)

(73) Assignee: GIANT FORCE TECHNOLOGY CORPORATION, New Taipei (TW)

( * ) Notice: Subject to any disclaimer, the term of this patent is extended or adjusted under 35 U.S.C. 154(b) by 80 days.

(21) Appl. No.: 14/779,279

(22) PCT Filed: Mar. 22, 2013

(86) PCT No.: PCT/CN2013/000336
§ 371 (c)(1),
(2) Date: Sep. 22, 2015

(87) PCT Pub. No.: WO2014/146218
PCT Pub. Date: Sep. 25, 2014

(65) Prior Publication Data
US 2016/0052905 A1    Feb. 25, 2016

(51) Int. Cl.
*A61K 38/21* (2006.01)
*A61K 45/06* (2006.01)
*A61K 31/215* (2006.01)
*A61K 31/713* (2006.01)
*C07D 307/88* (2006.01)
*A61K 31/5377* (2006.01)

(52) U.S. Cl.
CPC .......... *C07D 307/88* (2013.01); *A61K 31/215* (2013.01); *A61K 31/5377* (2013.01); *A61K 31/713* (2013.01); *A61K 38/21* (2013.01); *A61K 45/06* (2013.01)

(58) Field of Classification Search
CPC ...... A61K 38/21; A61K 45/06; A61K 31/215; A61K 31/713; C07D 307/88
See application file for complete search history.

(56) References Cited

U.S. PATENT DOCUMENTS

2009/0274771 A1* 11/2009 Watson .................. A61K 33/00
424/600

OTHER PUBLICATIONS

Smee et al., Antiviral Research, 2010, 88, 38-41.*
Oseltamivir, 2017, https://en.wikipedia.org/wiki/Oseltamivir.*
de Vries et al., PLOS Pathogens, 2013, 9(5), e1003343.*

* cited by examiner

*Primary Examiner* — Sun Jae Yoo
(74) *Attorney, Agent, or Firm* — WPAT, PC

(57) ABSTRACT

The present invention relates to a use of mycophenolate mofetil or a pharmaceutically acceptable salt thereof in the manufacture of a medicament against influenza virus. The present invention also relates to a use of mycophenolate mofetil or a pharmaceutically acceptable salt thereof in the manufacture of a medicament against drug-resistant influenza virus strains. The present invention is further related to a method for treating influenza in a subject, comprising administering to said subject an effective amount of mycophenolate mofetil or a pharmaceutically acceptable salt thereof.

6 Claims, 2 Drawing Sheets

USAGE OF MYCOPHENOLATE MOFETIL OR SALT THEREOF IN PREPARING DRUG FOR RESISTING AGAINST INFLUENZA VIRUS

FIELD OF THE INVENTION

The present invention relates to a use of mycophenolate mofetil or a pharmaceutically acceptable salt thereof in the manufacture of a medicament against influenza virus.

BACKGROUND OF THE INVENTION

Influenza viruses ("flu" for short) are one of the most threatening viruses against humans life. Four influenza pandemics occurred since the 20$^{th}$ century, respectively in 1918~1919 (Spanish flu, H1N1), 1957 (Asian flu, H2N2), 1968 (Hong Kong flu, H3N2) and 1977 (Russian flu, H1N1), of which the 1918 Spanish flu was the most serious pandemic, wherein its H1N1 viral strain was mutated from avian influenza and human influenza virus, and the influenza epidemic killed approximately 20 to 40 million people over the world. In 2009, an outbreak of a new strain of H1N1 influenza infected more than one million people in Mexico, the deaths of more than ten thousand people were estimated, and the H1N1 influenza virus continuously spreads (Neumann, G.; Noda, T.; Kawaoka, Y. Emergence and Pandemic Potential of Swine-Origin H1N1 Influenza Virus. *Nature.* 459: 931-939, 2009). In addition, a special attention should be given to the invasion of seasonal influenza A virus subtype H3N2, which was marked in the Annual Meeting on National Influenza Prevention and Control, China in 2010 as the viral strain resulting in a number of deaths in the past.

Influenza virus is a negative-sense single stranded RNA virus that causes influenza in human and animals, which belongs to the Orthomyxoviridae family and can be classified into three serotypes, A, B and C according to their difference in viral nucleoproteins, hereditary materials and matrix protein antigenic properties, wherein influenza A virus causes influenza between different hosts due to polymorphism of both hemagglutinin (HA) and neuraminidase (NA) on its viral surface. It is currently found that hereditary antigenic variation may occur in 16 types of HA (H1~16) and 9 NA (N1~N9); influenza B virus antigenic variation is less frequent and only causes regional infection; the main host of influenza C is swine, where the infection of influenza C in human is rare; thus, the above-mentioned worldwide scale influenza is an epidemic caused by influenza A virus.

Structure of influenza A virus from the outside to the inside can be divided into three parts, being the envelope, matrix proteins and core. There are around 500 spikes radially arranged towards the outside on the envelope, which are the two types of the above-mentioned antigen: rod-like spikes (HA) and mushroom-like spikes (NA). HA can adhere to the surfaces of animal red blood cells to bind to various the receptors thereon and induce agglutination. HA can divide into heavy chain and light chain after cleavage, which makes the virus fuse with its host cells. NA has mainly a sialic acid hydrolysis activity, which removes the last connection between the virus and the host cells, causing the virus to shed from the red blood cells it is adhered to, preventing aggregation of the virus, promoting its movement in the mucus. Matrix proteins are composed of M1 and M2, having an effect of protection to the core and maintenance of the viral structure. Additionally, the core is composed of 8 negative-sense single stranded RNA, wherein it entwines and combines with nucleoproteins and RNA polymerase (PB1, PB2 and PA) to form ribosomes. The reason influenza virus causes people's panic is mainly because its ways of variation results in new subtypes and catches us by surprise, wherein there are two ways of variation, one being antigenic shift, which is a small variation caused by point mutation of the antigen (NA) amino acid sequence of the influenza virus subtype; another being antigenic shift, which is the most common type of influenza virus variation, where large scale antigenic variation happens every ten years, caused by the host infected with two different virus strains at the same time and recombination of viral RNA forms new virus strains, resulting in a large impact (Hong-Shan Chen, Xing-Quan Zhang, Antivirus Drug: Methods and Applications, Chemical Industry Press, 328-311, 2006).

Influenza usually occurs in autumn, winter and early spring, wherein its attacking target is respiratory tract mucous epithelial cells, and it will reproduce in host cells, which leads to pathological changes such as mucous hyperemia, edema, cell degeneration and detachment. There are usually 1 to 3 days in the latent period, some symptoms such as fever, shivering, headache, nasal obstruction, body ache, will appear. When the virus spreads to the lower respiratory tract, it may lead to bronchitis and interstitial pneumonia. As influenza virus will reduce the ability of respiratory tract mucous epithelial cells to remove and adhere foreign bodies, it often causes secondary pneumonia, which is one of the main reasons of death by influenza (Morens, D. M.; Taubenberger, J. K.; Fauci, A. S. Predominant Role of Bacterial Pneumonia as a Cause of Death in Pandemic Influenza: Implications for Pandemic Influenza Preparedness. J. Infect. Dis. 198: 962-970, 2008).

Currently, the most adopted preventions and treatments of influenza are community isolation and supportive drug therapy, and therapeutic prevention can be further characterized to vaccines and antiviral agents. However, for viruses which continue to vary, protection by vaccines still has its risks; there are mainly three types of antiviral agents, the first type being M2 protein inhibitors, which act on viral transmembrane M2 ion channel, blocking H+ from entering the virus, making the viral envelope unable to fuse with the endosome, thus the virus is incapable to release its RNA, where the type of drugs are adamantan derivatives, such as amantadine and rimantadine; the second type being neuraminidase (NA) inhibitors, which act on neuraminidase, making the virus unable to hydrolyse sialic acid, thus unable to leave its host cell, blocking spreading of the virus, where the type of drugs includes oseltamivir (Tamiflu), zanamivir (Relenza), peramivir and cyclopentane or pyrrolidine derivatives; the third type being RNA polymerase inhibitors, which mainly inhibit the pathway of RNA polymerase for synthesizing viral proteins, where the drugs include 2'-deoxy-2'-fluoroguanosine (FdG) and T-705; alternatively, there are also treatments to prevent viral infection by utilizing interferons and siRNA (small interfering RNAs) (Clereq, E. D. Antiviral Agents Active against Influenza A Viruses. Not. Rev. Drug. Discov. 5: 1015-1025, 2006).

However, all the above-mentioned drugs are unable to achieve comprehensive inhibition against all types of influenza viruses, and have deficiencies, such as drug resistance and side effects Influenza A having highly varied antigens, is highly infectious, where around 500 million people get infected every year, often causing a high death rate, resulting in a heavy burden and economic loss to the society, thus active development of new antiviral agents is indeed an important task.

BRIEF SUMMARY OF THE INVENTION

It is first discovered in the invention that mycophenolate mofeteil or a salt thereof are effective against influenza virus.

Accordingly, in one aspect, the invention provides a use of mycophenolate mofetil or a pharmaceutically acceptable salt thereof in the manufacture of a medicament against influenza virus.

In one preferred embodiment of the invention, the pharmaceutically acceptable salt thereof may be hydrochloride salt, bromate salt, organic salt, and the like.

In another aspect, the medicament of the invention in combination with one or more anti-influenza virus drugs is also provided; wherein the anti-influenza virus agent is selected from the group consisting of a M2 inhibitor, a NA inhibitor, an RNA polymerase inhibitor, an interferon, and an siRNA.

In a preferred embodiment of the invention, the anti-influenza virus drug is (3R,4R,5S)-4-acetamide-5-amino-3-(1-ethylpropoxy)-1-cyclohexane)-1-carboxylic acid (oseltamivir phosphate; Tamiflu).

It is also unexpectedly found in the invention that mycophenolate mofetil or a salt thereof have anti-influenza virus effects against a drug-resistant influenza virus strain. Accordingly in one further aspect, the invention provides a use of mycophenolate mofetil or a pharmaceutically acceptable salt thereof in the manufacture of a medicament against a drug-resistant influenza virus strain.

In the invention, the drug-resistant influenza virus strains are drug-resistant variants of H1N1 or H3N2 viral strains. In a preferred embodiment of the invention, the drug-resistant influenza virus strain is a Tamiflu-resistant influenza viral strain.

The invention also provides a method for treating influenza in a subject, comprising administering to said subject an effective amount of mycophenolate mofetil or a pharmaceutically acceptable salt thereof. In one example of the invention, the subject to be administered is a subject infected with H1N1, H3N2 or a drug-resistant variant thereof. In a specific embodiment, the invention provides a method for treating influenza in a subject infected with a Tamiflu-resistant influenza viral strain. According to one embodiment of the invention, mycophenolate mofetil or a pharmaceutically acceptable salt thereof may be administered in combination with one or more anti-influenza virus agents. Other features of the invention will be clearly illustrated through the detailed description below, the examples and the claims.

BRIEF DESCRIPTION OF THE DRAWINGS

The aforementioned and the embodiments can be better described taken in conjunction with the annexed drawings. To better describe the invention, drawings of the suitable embodiments are listed hereof.

FIG. 1 provides an image showing the results of the immunofluorescence staining for determination of the effects of the drugs in different concentrations against a drug-resistant influenza viral strain by immunofluorescence staining.

FIG. 2 shows the results of the analysis for the effects of the test drugs against a drug-resistant influenza virus, wherein

DETAILED DESCRIPTION OF THE INVENTION

Figure 1:
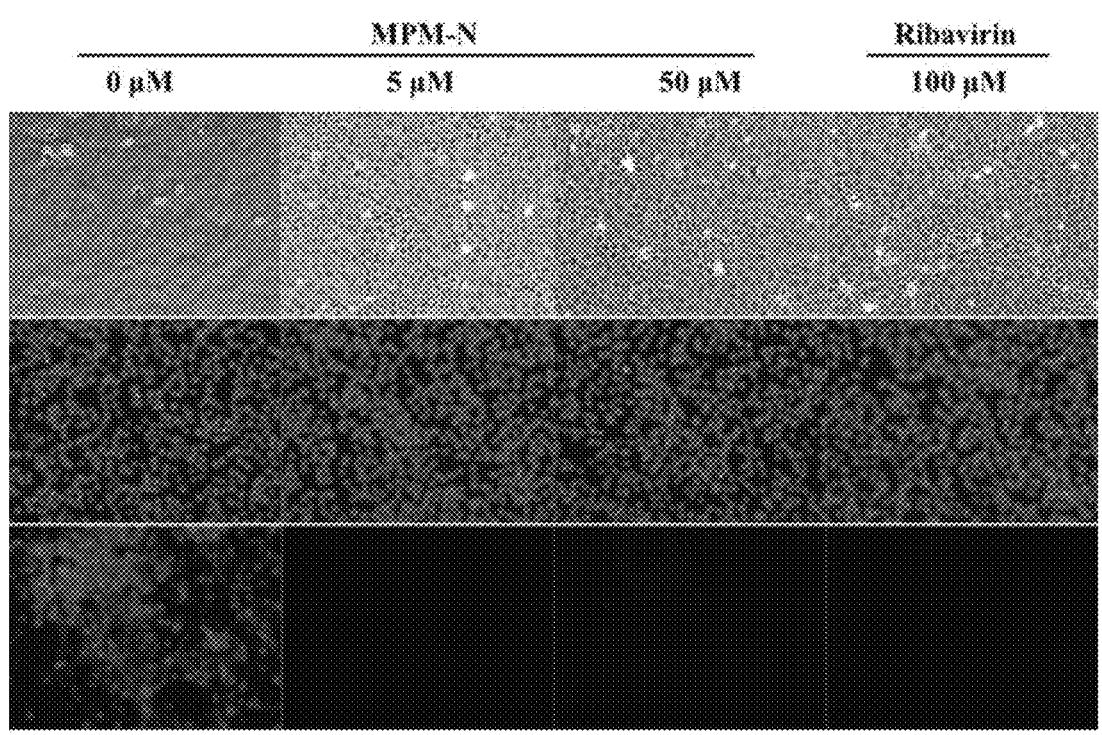
FIG. 1 provides an image showing the results of the immunofluorescence staining resulted from the detection of effects of agents in different concentrations against drug-resistant influenza viral strain by immunofluorescence staining.

Terms used in the description of the invention usually have the original meaning as that in the field of the invention, in the content of this invention, and the specific content where the terms are present.

The term "a" as used herein refers to the amount of at least one (one or more than one) unless specifically indicated otherwise.

The term "influenza virus" or "flu virus" that is the abbreviation for influenza virus, as used herein, refers to a negative-sense single stranded RNA virus that causes influenza in humans and animals which belongs to the Orthomyxoviridae family, classified into influenza A virus, influenza B virus and influenza C virus according to their difference in viral nucleoproteins, hereditary materials and matrix protein antigenic properties, and further classified into different subtypes according to the antigenicity of hemagglutinin and neuraminidase. According to the World Health Organization (WHO), six factors are considered for the nomenclature of influenza viral strains: antigenic type/host of origin/geographical origin/strain number/year of isolation (HnNn), wherein the host information is omitted for human influenza virus, and the subtype information is omitted for influenza B virus and influenza C virus. Influenza virus described in the invention includes influenza A virus, influenza B virus and influenza C virus. In a specific embodiment, influenza virus is H1N1, H3N2 or drug-resistant viral strains thereof, especially the viral strains with Tamiflu-resistance.

According to the invention, it is unexpectedly found that mycophenolate mofetil or a pharmaceutically acceptable salt thereof are effective against influenza virus. Accordingly, the invention provides a new use of mycophenolate mofetil or a pharmaceutically acceptable salt thereof in the manufacture of a medicament against influenza virus.

The term "mycophenolate mofetil" as used therein refers to 2-morpholinoethyl(E)-6-(1,3-dihydro-4-hydroxy-6-methoxy-7-methyl-3-oxo-5-isobenzofuranyl)-4-methyl-4-hexenoate, which has the structure below:

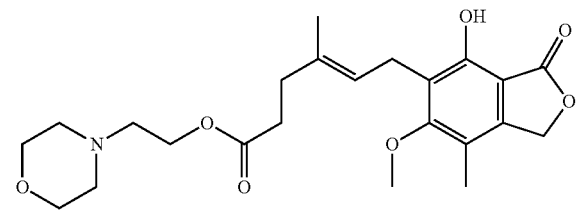 [SMILES: COc1c(C)c2c(c(O)c1C/C=C(\C)CCC(=O)OCCN1CCOCC1)C(=O)OC2]

The term "pharmaceutically acceptable salt thereof" as used therein refers to a salt of a compound that are safe and effective for human and animal's intake, which has the desired bioactivity as the same as the compound. In the invention, pharmaceutically acceptable salt of mycophenolate mofetil includes but is not limited to an acidic salt or a basic salt of mycophenolate mofetil. For example, the acidic salt may be synthesized with hydrochloric acid, hydrobromic acid, iodic acid, sulfuric acid, sodium bisulfate, phosphoric acid, phosphate, acetic acid, lactic acid, salicylic acid, citric acid, tartaric acid, pantothenic acid, tartrate, ascorbic acid, succinic acid, maleic acid, fumaric acid, gluconic acid, formic acid, benzoic acid, glutamic acid, methanesulfonic acid, or para-toluene sulfonic acid, The basic salt may be synthesized with aluminum, calcium, lithium, magnesium, potassium, sodium, zinc or diethanolamine.

In a preferred example of the invention, the pharmaceutically acceptable salt is a hydrochloride salt.

In the invention, the mycophenolate mofetil may be administered in combination with one or more anti-influenza virus drugs, including but not limited to an M2 protein inhibitor such as adamantane derivative like amantadine or rimantadine; a neuraminidase (NA) inhibitor such as oseltamivir (Tamiflu), zanamivir (Relenza), peramivir or cyclopentane or pyrrolidine derivative; an RNA polymerase inhibitor such as 2'-deoxy-2'-fluoroguanosine (FdG), T-705; and interferon or siRNA and etc.

In another preferred example of the invention, the above-mentioned anti-influenza virus drug is Tamiflu, which is (3R,4R,5S)-4-acetamide-5-amino-3-(1-ethylpropoxy)-1-cyclohexane)-1-carboxylic acid (oseltamivir phosphate). According to the invention, the medicament may be administered through parenteral or oral route. The forms of the medicament for parenteral administration include a solution, suspension, emulsion, and solid injectable composition that are dissolved or suspended in a solvent immediately before use. The formulation for injection may be prepared by dissolving, suspending or emulsifying one or more of the drugs in a diluent. Examples of said diluents are distilled water for injection, physiological saline, vegetable oil, alcohol, and a combination thereof. Further, the formulation for injection may contain stabilizers, solubilizers, suspending agents, emulsifiers, soothing agents, buffers, preservatives, etc. The formulation for injection may be sterilized in the final step or prepared by sterile procedure. The medicament of the invention can also be formulated as sterile solid formulations, for example, by lyophilizing, and can also be sterilized immediately before use or dissolved in injectable sterile water or other sterile diluents. The medicament can also be administered orally, wherein the composition can be in solid or liquid form. The solid forms include tablets, pills, capsules, dispersible powders, granules, and the like. The oral pharmaceutical compositions may also include gargles and sublingual tablets. The capsules include hard capsules and soft capsules. In such solid compositions for oral administration, one or more of the drug (s) may be admixed solely or with diluents, binders, disintegrators, lubricants, stabilizers, solubilizers, and then formulated into a preparation in a conventional manner. When necessary, such preparations may be coated with a coating agent, or they may be coated with two or more coating layers. On the other hand, the liquid forms of compositions for oral administration include pharmaceutically acceptable aqueous solutions, suspensions, emulsions, syrups, elixirs, and the like. In such compositions, one or more of the active compound(s) may be dissolved, suspended or emulsified in a commonly used diluent (such as purified water, ethanol or a mixture thereof, etc.). Besides such diluents, said compositions may also contain wetting agents, suspending agents, emulsifiers, sweetening agents, flavoring agents, perfumes, preservatives and buffers and the like.

In the invention, it is unexpectedly found that mycophenolate mofeteil or a salt thereof are effective against drug-resistant influenza virus strains. Accordingly, the invention provides a use of mycophenolate mofeteil or a salt thereof in the manufacture of a medicament against drug-resistant influenza virus stains.

In the invention, the drug-resistant influenza virus strains are drug-resistant variants of H1N2 or H3N2 viral strains. In one specific embodiment, the drug-resistant influenza virus strain is a Tamiflu-resistant influenza viral strain.

The invention also provides a method for treating influenza in a subject, comprising administering to said subject an effective amount of mycophenolate mofetil or a pharmaceutically acceptable salt thereof. In one example of the invention, the subject is a subject infected with a Tamiflu-resistant influenza viral strain.

The term "treatment" as used herein refers to applying or administering a composition comprising one or more active agents to a subject having a disorder, symptoms of the disorder or tendency of having the disorder to cure, heal, alleviate, ease, transform, rectify, ameliorate, improve or affect the disorder, symptoms of the disorder, disabilities caused by the disorder or tendency of having the disorder.

The term "effective amount" as used herein refers to when compared to subjects not receiving said amount, the treating, healing, preventing or ameliorating effects on a disorder, a disease or a side effect which medicaments and agents may achieve, or the reduction of the development rate of a disorder or a disease. The term also covers the effective amount for promoting normal physiological function. The therapeutically effective amount of a medicament or an agent is decided by many factors. For example, the age and weight of an animal, the actual condition which is in need for treatment and its severity, the characteristics of the formulation and the route of administration are all factors to be considered.

The terms "subject", "target" and "patient" used herein can be used interchangeably, which refers to any mammal that is in need for treatment or medical care, specifically humans. Other subjects may include cows, dogs, cats, guinea pigs, rabbits, rats, mice, horse, and the like.

According to the invention, mycophenolate mofetil or a pharmaceutically acceptable salt thereof may be used in combination with one or more anti-influenza virus drugs. The drug may be selected from the group consisting of an M2 inhibitor, an NA inhibitor, an RNA polymerase inhibitor, an interferon, and an siRNA. In a preferred embodiment of the invention, the drungt is (3R,4R,5S)-4-acetamide-5-amino-3-(1-ethylpropoxy)-1-cyclohexane)-1-carboxylic acid (oseltamivir phosphate; i.e., Tamiflu). According to the invention, the medicament may be used in combination by mixing the medicament in the same formulation, or placed in different formulations separately, such as separate capsules, tablets, pastilles, injectants. They can be applied at the same time (simultaneously) or sequentially. In one example, mycophenolate mofetil or a pharmaceutically acceptable salt thereof is administered orally to a subject simultaneously with oseltamivir phosphate.

Without further elaboration, it is believed that one skilled in the art can, based on the descriptions, utilize the present invention to its fullest extent. The specific example below is to be construed as merely illustrative, and not limitative of the remainder of the disclosure in any way whatsoever.

EXAMPLES

Materials for Cell Pharmacology Test and Immunostaining

Cell line: MDCK: Madin-Darby canine kidney cells.
Culture medium:
1. 10% Fetal bovine serum (FBS);

2. TPCK (tosylsulfonyl phenylalanyl chloromethyl ketone-treated trypsin);

3. DMEM (Dulbcco's modified Eagle medium).

Cell buffer: Phosphate-buffer saline (PBS).

Viral strain: Influenza A (H1N1/H3N2) (provided by Professor Chen-Wen Yao, Department of Pathology, Tri-Service General Hospital, Taiwan).

ELISA reader: BIOTEK CERES 900 EIR READER. Host cell survival rate is determined by MTT assay.

Materials for Animal Trial

Six-week old male BALB/c mice, purchased from Bio-LASCO Taiwan Co., Ltd.

Example 1. Preparation of Mycophenolate Mofetil (MPM) and a Hydrochloride Salt Thereof (MPM-N)

Mycophenolate mofetil can be prepared according to the method as described below: 3.2 g (10 mmol) mychphenolic acid in ice bath was dissolved into 30 ml dichloromethane solution, 1.5 ml (17.5 mmol) oxalyl chloride and two drops of dimethylformamide was added, and the mixture was stirred for 3 hours under room temperature. The mixture was vacuum-evaporated to obtain compound 11b. The preparation process is as follows:

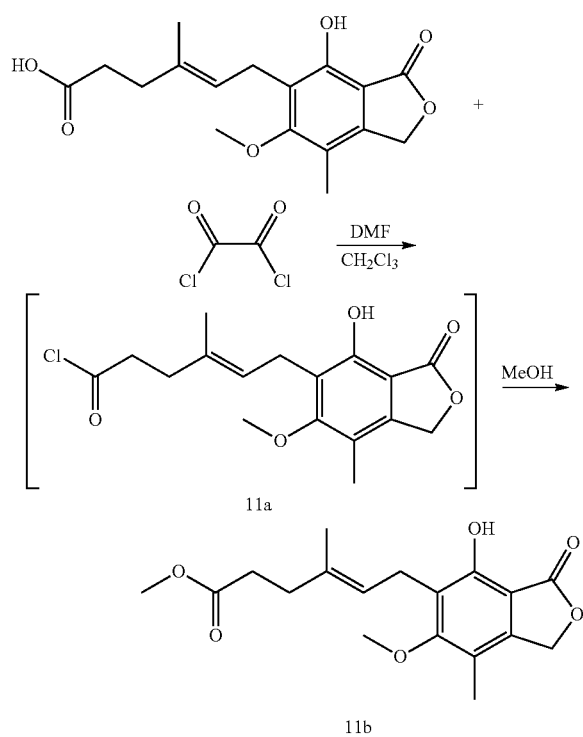

Compound 11b was dissolved into 20 ml ethyl acetate solution, 2.6 ml (20 mmol) 4-(2-hydroxyethyl) morpholine was added, the mixture was stirred under room temperature for 30 minutes and vacuum-evaporated and crude product of mycophenolate mofetil was obtained, then 50 ml water was added and neutralization was done with 0.1 N hydrochloric acid to reach pH 7.0 to facilitate precipitation of pure mycophenolate mofetil compound (4.7 g, 81.0%, mp. 95-96° C.).

Mycophenolate mofetil hydrochloride can be prepared according to the method mentioned below: 2 g (4.61 mmol) mycophenolate mofetil was dissolved in 50 ml ethyl acetate solution under room temperature, the mixture was stirred and added with 0.3 ml (1.2 equivalence) of acetic acid and 0.7 ml (1.2 equivalence) of trimetyhylchlorosilane, the mixture was then stirred for 1 hour and precipitation was filtered, where the solid matter was washed with ethyl acetate thrice under room temperature and vacuum-evaporated to obtain 2.11 g mycophenolate mofetil hydrochloride (97.6%, mp. 157.2° C.).

Example 2. Determination for Minimal Inhibitory Concentration and Toxicity of the Purified Compounds Anti-viral activity test was conducted by determining the level of virus infection in host cells through the host cell survival rate. The host cell survival rate was analysed with MTT assay, based on the theory that 3-(4,5-dimethylthiazol-2-yl)-2,5-diphenyltetrazolium bromide (MTT) yellow solution solids can be metabolized by the dehydrogenases in the mitochondria of live cells, and reduce the tetrazolium ring to form purple insoluble precipitation formazan (3-(4,5-dimethylthiazol-2-yl)-2,5-diphenyl-formazan) and accumulate in the cells. Since only dehydrogenases in live cells have catalysing activity, the absorbance value measured will be proportional with the number of live cells. In this example, the yield of formazan was measured to assess the survival rate of cells.

In the example, H1N1 and H3N2 were specifically used as viral strains to test the anti-influenza virus activity as detailed below:

I. Cell Culture

The cells were cultured in 37° C., 5% $CO_2$ incubator after thawing, when the cells were around 80% confluent, PBS was used to wash the cells, trypsin was added and allowed to react for 5 minutes to detach the cells attached to the dish, DMEM was added to neutralize trypsin reaction and they were centrifuged (1200 rpm, 5 minutes), the supernatant was suction-removed, the cells were homogenized with a small amount of culture medium, then the cells were counted and diluted with DMEM to the cell concentration required for the experiments on anti-influenza virus activity.

II. Experimental Procedures

1. The cells were diluted to a designated concentration ($2\times10^4$ cells/well) and seeded into 96-well plate, then cultured in 37° C., 5% $CO_2$ incubator for 20~24 hours.

2. Each well was washed with 100 μl cell buffer (PBS) twice, and lastly added with 100 μg/well TPCK culture medium, then placed into the incubator, and treated with the drugs to be tested after diluted.

3. The samples were divided into five groups treated with D+V, D, V, Mock and Blank respectively, they were then cultured in 37° C., 5% $CO_2$ incubator for 48 hours;

4. Two days later, cell apoptosis condition was examined; MTT assay was performed, 20 μl (5 mg/ml) MTT reagent was added to each of the groups treated with D+V, D, V, Mock and Blank and incubated for 5 hours;

5. The culture medium was suction-removed, 25 μl glycine buffer and 100 μl dimethyl sulfoxide (DMSO) were added to the groups treated with D+V, D, V, Mock and Blank.

The plates were read for absorbance at 40 nm.

III. Administration Condition

1. D+V: 50 μl of drugs to be tested in different concentrations and 50 μl of influenza virus (0.01 MOI) were given at the same time;
2. D: 50 μl of drugs to be tested in different concentrations and 50 μl TPCK culture medium were given;
3. V: 50 μl of influenza virus (0.01 MOD and 50 μl TPCK culture medium were given;
4. Mock: includes 100 μl MDCK cells and TPCK culture medium;
5. Blank: does not include MDCK cells and TPCK culture medium.

IV. Influenza Virus (H1N1/H3N2/WSN) Infective Dose 0.01 MOI (multiplicity of infection) of influenza viral strain was given.

V. Concentration of Drugs to be Tested

The purified compounds in the eight different concentrations: 100 μg/ml, 50 μg/ml, 25 μg/ml, 12.5 μg/ml, 6.25 μg/ml, 1.563 μg/ml, 0.391 μg/ml and 0.098 μg/ml.

VI. Positive Control

Anti-virus agent Ribavirin.

VII. Readings of MTT Assay Result

1. Cell survival rate:

$$\frac{(D+V/D/V) - \text{Blank}}{\text{Mock}} \times 100\%$$

2.0~25% cell survival is recorded as +/−;
25~50% cell survival is recorded as +;
50~75% cell survival is recorded as ++;
75~100% cell survival is recorded as +++;
>100% cell survival is recorded as ++++.

When the drug to be tested was recorded as "+++" or above, it was considered a drug effective to cell apoptosis. Each of the groups had two or more repeats.

Referring to Table 1, all of mycophenolate mofetil (MPM) and a hydrochloride salt thereof (MPM-N) in the concentrations from 100 μg/ml to 0.391 μg/ml showed the survival rate at 75% in MDCK cells, and were nontoxic to cells in the anti-H1N1 influenza virus activity test.

TABLE 1

Minimal inhibitory concentration against influenza virus (H1N1) and drug toxicity of the compounds

| | MPM | | MPM-N | | Ribavirin* | |
|---|---|---|---|---|---|---|
| | D + V | D | D + V | D | D + V | D |
| 100 μg/ml | +++ | +++ | +++ | ++++ | ++++ | ++++ |
| 50 μg/ml | +++ | +++ | +++ | +++ | ++++ | ++++ |
| 25 μg/ml | +++ | +++ | +++ | +++ | ++++ | ++++ |
| 12.5 μg/ml | +++ | +++ | +++ | +++ | ++++ | ++++ |
| 6.25 μg/ml | +++ | +++ | +++ | +++ | +++ | ++++ |
| 1.563 μg/ml | +++ | +++ | +++ | +++ | + | ++++ |

TABLE 1-continued

Minimal inhibitory concentration against influenza virus (H1N1) and drug toxicity of the compounds

| | MPM | | MPM-N | | Ribavirin* | |
|---|---|---|---|---|---|---|
| | D + V | D | D + V | D | D + V | D |
| 0.391 μg/ml | ++++ | ++++ | ++++ | ++++ | + | ++++ |
| 0.098 μg/ml | ++ | ++++ | ++ | ++++ | + | ++++ |

*Ribavirin is the control.

TABLE 2

Minimal inhibitory concentration against influenza virus (H3N2) and drug toxicity of each compound

| | MPM | | MPM-N | | Ribavirin* | |
|---|---|---|---|---|---|---|
| | D + V | D | D + V | D | D + V | D |
| 100 μg/ml | +/− | ++++ | +/− | ++++ | ++++ | ++++ |
| 50 μg/ml | +++ | +++ | +++ | ++++ | ++++ | ++++ |
| 25 μg/ml | +++ | +++ | +++ | ++++ | ++++ | ++++ |
| 12.5 μg/ml | +++ | +++ | +++ | ++++ | ++++ | ++++ |
| 6.25 μg/ml | +++ | +++ | ++++ | ++++ | +++ | ++++ |
| 1.563 μg/ml | +++ | +++ | +++ | +++ | +/− | ++++ |
| 0.391 μg/ml | + | ++++ | + | ++++ | +/− | ++++ |
| 0.098 μg/ml | +/− | ++++ | +/− | ++++ | +/− | ++++ |

*Ribavirin is the control.

In the tests for antiviral activity against WSN influenza virus, the inhibitory effects of mycophenolate mofetil (MPM) and a hydrochloride salt thereof (MPM-N) in different concentrations were shown in Table 3, indicating that mycophenolate mofetil and hydrochloride salt thereof were active against anti-influenza virus in the concentrations from 100 μg/ml to 0.098 μg/ml.

TABLE 3

| | MPM | | MPM-N | | Ribavirin* | |
|---|---|---|---|---|---|---|
| | D + V | D | D + V | D | D + V | D |
| 100 μg/ml | ++++ | ++++ | ++++ | ++++ | ++++ | ++++ |
| 50 μg/ml | ++++ | ++++ | ++++ | ++++ | ++++ | ++++ |
| 25 μg/ml | ++++ | ++++ | ++++ | ++++ | ++++ | ++++ |
| 12.5 μg/ml | ++++ | ++++ | ++++ | ++++ | +++ | ++++ |
| 6.25 μg/ml | ++++ | ++++ | ++++ | ++++ | ++++ | ++++ |
| 1.563 μg/ml | ++++ | ++++ | ++++ | ++++ | ++++ | ++++ |
| 0.391 μg/ml | ++++ | ++++ | ++++ | ++++ | + | +++ |
| 0.098 μg/ml | ++++ | +++ | ++++ | +++ | + | +++ |

*Ribavirin was used as the control.

Example 3. Minimal Inhibitory Concentration Against Drug-Resistant Virus Strains The minimal inhibitory concentration (MIC) of the following compounds against drug-resistant influenza virus variants were determined according to the above-mentioned method.
MPM: mycophenolate mofetil
MPM-N: hydrochloride
Tested influenza viral strains include:
H1N1 T.R.—Tamiflu-resistant variant of H1N1 viral strain was obtained by variation of Influenza A virus (H1N1), which was found to be similar to Influenza A/Taiwan/937/2009 after sequencing.
H3N2—Influenza A viral strain (H3N2), which was found to be similar to Influenza A/New York/469/2004 after sequencing.

WSN—Influenza A/WSN/33 (H1N1), which was found to be similar to Influenza A/Hong Kong/470/97 after sequencing.
Influenza B—Influenza B viral strain.
H1N1—Influenza A viral strain (H1N1).

TABLE 4

Comparison of the 50% effective concentration ($EC_{50}$), the 50% cytotoxic concentration ($CC_{50}$) and the selection index (S.I.) between different drugs

| Compound | Condition | H1N1 T.R. $EC_{50}$ | H1N1 WSN $EC_{50}$ | H3N2 $EC_{50}$ | S.I. |
|---|---|---|---|---|---|
| Ribavirin* | D + V | 3.125 | 3.125 | 12.5 | >16 |
| MPM | D + V | 0.391 | 0.098 | 1.560 | |
| | D1 + V | 0.391 | 0.098 | 1.560 | |
| | V1 + D | 0.391 | 0.098 | 1.560 | |
| | D | >200 | >200 | >200 | >2000 |
| MPM-N | D + V | 0.391 | 0.049 | 1.560 | |
| | D1 + V | 0.391 | 0.049 | 1.560 | |
| | V1 + D | 0.391 | 0.049 | 1.560 | |
| | D | >200 | >200 | >200 | >4000 |

*Ribavirin is the control.
$EC_{50}$: 50% effective concentration,
$CC_{50}$: 50% cytotoxic concentration,
Selection Index (S.I.): $CC_{50}/EC_{50}$.

As shown in Table 4, it is indicated that mycophenolate mofetil (MPM) and a hydrochloride salt thereof (MPM-N) both had better minimal inhibitory concentrations against the drug-resistant virus strains as compared to the group treated with Ribavirin as control.

TABLE 5

Comparison of minimal inhibitory concentrations against drug-resistant influenza viral strains between different drugs

| | Minimal Inhibitory Concentration (MIC) (µg/ml) | | | | |
|---|---|---|---|---|---|
| | H1N1 T.R. | H3N2 | WSN | Inf B | H1N1 |
| MPM | 0.39 | 1.56 | 0.097 | | 0.195 |
| MPM-N | 0.39 | 1.56 | 0.0488 | | |

It is confirmed according to the results in table 5, mycophenolate mofetil (MPM) and a hydrochloride salt thereof (MPM-N) have good effects against drug-resistant influenza viral strains.

Example 4. MPM-N Effectively Inhibits Tamiflu-Resistant Viral Strain rWSN$^{H274Y}$ To evaluate the effects of mycophenolate mofetil hydrochloride (MPM-N) against drug-resistant influenza viral strains, viral core proteins were detected by the cell immunofluorescence staining to confirm whether the drug is effective against the viral infection. Specifically, Tamiflu-resistant H1N1 viral strain rWSN$^{H274Y}$ was chosen for the test in this example.

Referring to FIG. 1, it was shown by the immunofluorescence staining that 100 µM Ribavirin was required to inhibit Tamiflu-resistant viral strain rWSN$^{H274Y}$, as compared to mycophenolate mofetil hydrochloride (MPM-N) in the concentration of 5 µM, which surpassed Ribavirin.

Example 5. The Use of MPM-N Alone or in Combination Effectively Increased Survival Rate of Influenza Virus Infected Mice Influenza virus infected mouse animal model was used to analyse the survival rate and evaluate the anti-influenza virus effect of each of the compounds. H1N1 WSN viral strain was used in the anti-influenza virus animal test in this example. Six-week old male BALB/c mice were anesthetized with Zoletil and infected with $1\times10^3$ PFU of virus by intranasal injection (i.n.) and administered with drugs orally. Administration conditions can be divided into (1) the control group treated with viral infection only; (2) the group treated with viral infection and Tamiflu, 0.1 mg/kg, for 7 consecutive days; (3) the group treated with viral infection and Tamiflu, 1 mg, for 7 consecutive days; (4) the group treated with viral infection and MPM-N, 0.3 mg, for 7 consecutive days; and (5) the group treated with viral infection and 0.1 mg/kg Tamiflu and 0.3 mg MPM-N, for 7 consecutive days.

Figure 2A:
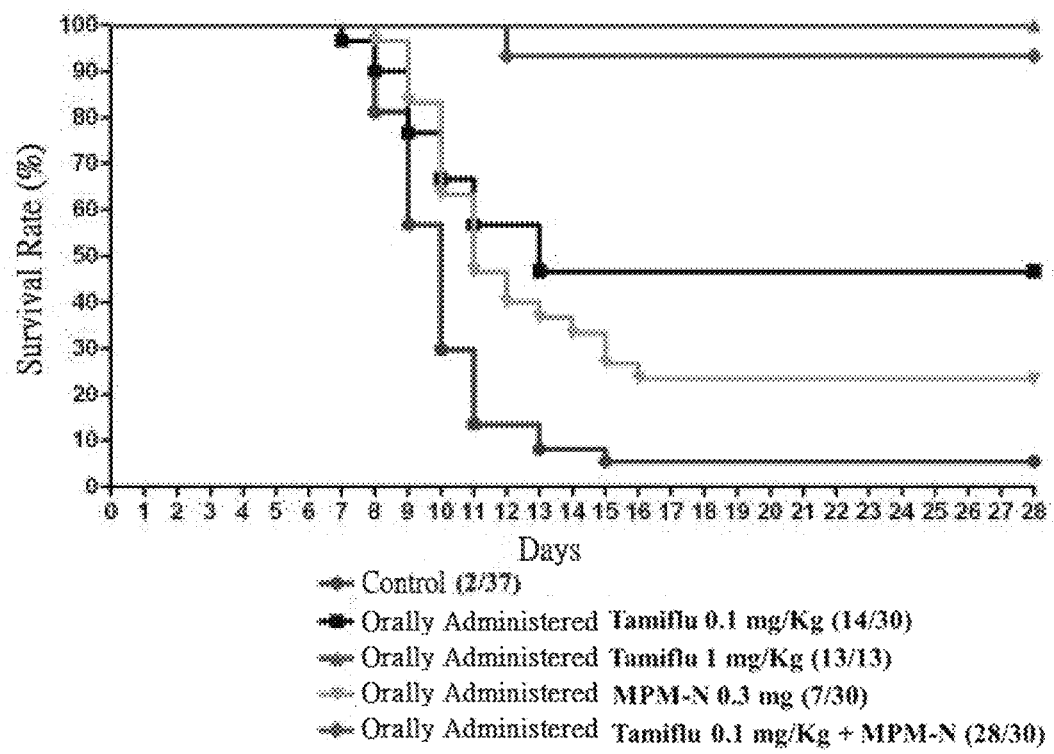
FIG. 2(A) shows the survival rate of the mouse treated with the test drugs in different conditions.
Figure 2B:
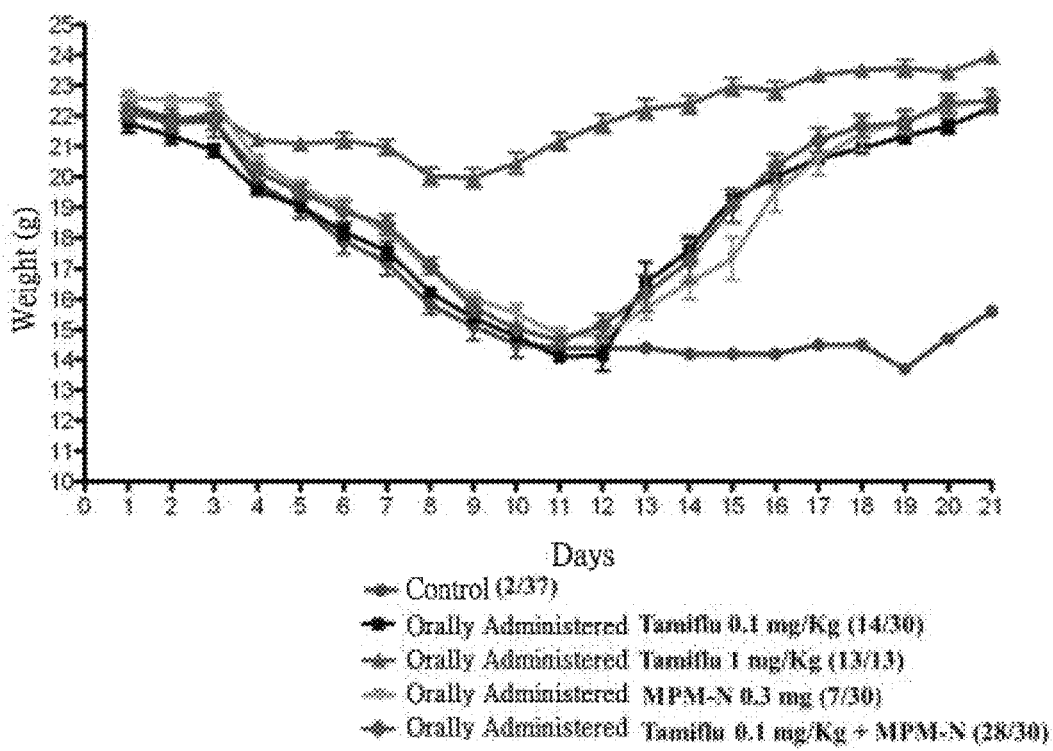
FIG. 2(B) shows the changes of the test mouse's body weights.

The survival rate of each group was observed and the mice' body weight change was measured after infection of influenza virus. As shown in FIGS. 2(A) and 2(B), the results of the study confirmed that the survival rate of mice without taking any drugs was only 5.4% (2/37), while the survival rate of the mice was raised to 23.3% (7/30) when MPM-N was treated alone, mice, the survival rate was 46.7% (14/30) when a low dosage of Tamiflu alone was treated, the survival rate was 100% (13/13) when a high dosage of Tamiflu was treated, and the survival rate was greatly increased to 93.3% (28/30) when a low dosage of Tamiflu (0.1 mg/kg) and MPM-N (0.3 mg) was treated. It was concluded that MPM-N, either administration alone or in combination with other anti-flu drugs, showed a great effect against influenza virus.

Although the present invention is disclosed through preferred embodiments as shown above, it is not in any way to limit the present invention, and persons skilled in the art of the present invention should be able to utilize the present invention to its broadest scope through modification and retouch based on the descriptions herein without deviating from the spirit and scope of the present invention, which should belong to the scope of protection defined in the claims of the present invention.

We claim:

1. A method for inhibiting an infection of influenza virus, comprising administering to a subject an effective amount of mycophenolate mofetil or a pharmaceutically acceptable salt thereof, wherein the infection of influenza virus is caused by a drug-resistant variant of influenza virus.

2. The method according to claim 1, wherein the drug-resistant variant of influenza virus is a drug-resistant variant of H1N1 or H3N2.

3. The method according to claim 1, wherein the drug-resistant variant of influenza virus is resistant to (3R, 4R, 5S)-4-acetamide-5-amino-3-(1-ethylpropoxy)-1-cyclohexane)-1-carboxylic acid (oseltamivir phosphate).

4. The method according to claim 1, wherein the mycophenolate mofetil or a pharmaceutically acceptable salt thereof is used in combination with one or more anti-influenza virus drug selected from the group consisting of a M2 inhibitor, a NA inhibitor, an RNA polymerase inhibitor, an interferon, and a siRNA.

5. The method according to claim 1, wherein the mycophenolate mofetil or a pharmaceutically acceptable salt thereof is used in combination with (3R, 4R, 5S)-4-acetamide-5-amino-3-(1-ethylpropoxy)-1-cyclohexane)-1-carboxylic acid (oseltamivir phosphate).

6. The method according to claim 1, wherein the pharmaceutically acceptable salt is hydrochloride salt.

* * * * *